US 8,290,579 B2

(12) United States Patent
Domb (10) Patent No.: US 8,290,579 B2
(45) Date of Patent: Oct. 16, 2012

(54) DEVICE, METHODS AND SPONGES FOR IONTOPHORETIC DRUG DELIVERY (75) Inventor: Abraham J. Domb, Efrat (IL)

(73) Assignee: Yissum Research Development Company of the Hebrew University of Jerusalem, Ltd., Jerusalem (IL)

( * ) Notice: Subject to any disclaimer, the term of this patent is extended or adjusted under 35 U.S.C. 154(b) by 1526 days.

(21) Appl. No.: 10/546,204

(22) PCT Filed: Feb. 19, 2004

(86) PCT No.: PCT/IL2004/000167
§ 371 (c)(1),
(2), (4) Date: Mar. 13, 2006

(87) PCT Pub. No.: WO2004/073794
PCT Pub. Date: Sep. 2, 2004

(65) Prior Publication Data
US 2006/0161097 A1 Jul. 20, 2006

Related U.S. Application Data (60) Provisional application No. 60/447,713, filed on Feb. 19, 2003.

(51) Int. Cl.
*A61N 1/30* (2006.01)
(52) U.S. Cl. ........................................ 604/20
(58) Field of Classification Search .............. 604/19–22, 604/890.1, 891.1; 600/397, 391, 396, 392, 600/383; 607/141, 53, 44, 149, 152
See application file for complete search history.

(56) References Cited

U.S. PATENT DOCUMENTS

| 4,149,533 | A |   | 4/1979 | Ishikawa et al. |
| 4,250,878 | A | * | 2/1981 | Jacobsen et al. ............... 604/20 |
| 5,087,243 | A |   | 2/1992 | Avitall |
| 5,222,936 | A |   | 6/1993 | Stephen et al. |
| 5,298,017 | A | * | 3/1994 | Theeuwes et al. .............. 604/20 |
| 5,401,239 | A |   | 3/1995 | Stephen et al. |

(Continued)

FOREIGN PATENT DOCUMENTS
EP 0 774 272 5/1997
(Continued)

OTHER PUBLICATIONS

Nicoli S. et al.: "Design of triptorelin loaded nanospheres for transdermal iontophoretic administration". Int. J. of Pharmaceutics, vol. 214, 2001, pp. 21-35, XP002285730.

(Continued)

*Primary Examiner* — Manuel Mendez
(74) *Attorney, Agent, or Firm* — Vorys, Sater, Seymour and Pease LLP; Susanne M. Hopkins (57) ABSTRACT

Disclosed are devices and methods for administration of charged drugs to tissues of the oral cavity and for intra-tissue administration.
The disclosed drug applicator for intra-tissue use includes an introducer such as a needle or catheter that is adapted to penetrate into a living tissue. The introducer has a drug-providing portion, and the applicator has current-generating element to pass through it an electrical current. Passing an electrical current through the drug-providing portion causes the drug to eject into treated tissue.
Also disclosed are charged drugs suitable for iontophoretic administration, which include a bioactive agent encapsulated in charged nano-particles.

18 Claims, 4 Drawing Sheets

U.S. PATENT DOCUMENTS

| | | | |
|---|---|---|---|
| 5,486,160 A | 1/1996 | Rossi et al. | |
| 5,558,961 A | 9/1996 | Doeff et al. | |
| 5,720,720 A | 2/1998 | Laske et al. | |
| 5,728,068 A | 3/1998 | Leone et al. | |
| 5,743,016 A | 4/1998 | Manne et al. | |
| 5,833,647 A | 11/1998 | Edwards | |
| 5,843,016 A | 12/1998 | Lugnani et al. | |
| 5,908,400 A * | 6/1999 | Higo et al. | 604/20 |
| 6,006,130 A | 12/1999 | Higo et al. | |
| 6,048,545 A * | 4/2000 | Keller et al. | 424/450 |
| 6,159,445 A * | 12/2000 | Klaveness et al. | 424/9.6 |
| 6,219,557 B1 | 4/2001 | Havinis | |
| 6,232,441 B1 | 5/2001 | Wu et al. | |
| 6,532,386 B2 * | 3/2003 | Sun et al. | 604/20 |
| 6,564,093 B1 * | 5/2003 | Ostrow et al. | 604/20 |
| 6,706,032 B2 * | 3/2004 | Weaver et al. | 604/500 |
| 2002/0183685 A1 | 12/2002 | Crawford et al. | |

FOREIGN PATENT DOCUMENTS

| | | |
|---|---|---|
| WO | 94/05361 | 3/1994 |
| WO | 97/04832 | 2/1997 |
| WO | 99/40967 | 8/1999 |
| WO | 01/12260 | 2/2001 |

OTHER PUBLICATIONS

Kostouros G. et al.: "Facilitated diffusion by iontophoresis of vasoactive agents to the rat incisor pulp". Eur. J. of Oral Sci., vol. 104, 1996, pp. 570-576.

McBride M. et al.: "The effectiveness of sodium fluoride iontophoresis in patients with sensitive teeth". Quintessence Int., vol. 22, 1991, pp. 637-640.

Kostouros G. et al.: "The blocking effect of iontophoretic administration of lidocaine on neurogenic vascular reactions in rat dental pulp". Eur. J. of Oral Sci., vol. 104, 1996, pp. 577-582.

Dumitriu S. et al.: "Hydrogel and General Properties of Biomaterials". pp. 3-97.

* cited by examiner

DEVICE, METHODS AND SPONGES FOR IONTOPHORETIC DRUG DELIVERY

CROSS-REFERENCE

This is a National Phase Application filed under 35 U.S.C. 371 of International Application No. PCT/IL2004/000167, filed Feb. 19, 2004, claiming the benefit under 35 USC 119(e) of U.S. Provisional Application No. 60/447,713, filed Feb. 19, 2003, the entire contents of each of which is hereby incorporated herein by reference in its entirety.

FIELD OF THE INVENTION

This invention relates to methods, devices and sponges for iontophoretic drug delivery.

BACKGROUND OF THE INVENTION

Iontophoresis (hereinafter INT) is a method for transdermal delivery of charged drugs by using electricity as external stimulation. It is based on movement of charged molecules under electrical potential, such that in an electrical field generated between an anode and a cathode, molecules with a positive charge move from the anode to the cathode, while those with a negative charge move from the cathode to the anode. This movement promotes penetration of the charged molecules through a skin barrier.

The inventor of the present invention has already invented a method and a device for INT administration of drugs to the eye (see WO 99/40967).

The present invention discloses methods and devices to apply INT to the oral cavity. Some related art may be found in U.S. Pat. No. 4,149,533, which relates to a device for iontophoretic application of fluoride on tooth, and U.S. Pat. No. 6,006,130, which relates to an INT electrode which is applicable to mucous membranes and oral mucous membranes.

The present invention also discloses methods and devices to apply INT into a tissue present within the living bodies of animals, mammals, or humans. Related art may be found in U.S. Pat. No. 5,720,720, which discloses a convection-enhanced delivery catheter and method adapted to increase the migration distance of the infused drug by maintaining a pressure gradient during interstitial infusion.

Further related art may be found in U.S. Pat. Nos. 5,087,243; 5,222,936; 5,232,441; 5,401,239; 5,486,160; 5,588,961; 5,728,068; 5,843,016 and 6,219,557, and in WO 94/05361, all of which describe various types of iontophoretic systems for insertion into hollow, tubular body cavities, such as bladder, uterus, urethra, and blood vessels.

Additional related art may be found in:
Kostouros et al., Eur. J. Oral Sci. 104, 1996, 570-576 and 577-582;
M. A. McBride et al., Quintessencde Int. 22, 1991, 637-640; and
Nicoli et al., International Journal of Pharmaceutics, 214 (1-2), pp. 31-35, 2001;
which describe preparation of nano-particles, of the kind that may find use in methods and devices according to the present invention.
Dumitriu, S., Polymeric Biomaterials, (Editor) Marcel Dekker, NY, 3-85, 1993; describes hydrogels, which may be useful in accordance with the invention.

SUMMARY OF THE INVENTION

The present invention provides according to a first aspect thereof a method for the administration of charged drug to a tissue comprising contacting said tissue with a sponge loaded with said charged drug and passing a current through the sponge in a direction that moves the charged drug towards the tissue, characterized in that said charged drug includes charged nanoparticles encapsulating a bioactive agent.

The invention further provides a sponge impregnated with charged nanoparticles that encapsulate a bioactive agent and a method for the preparation thereof, the method comprising swelling a dry sponge material with a dispersion of nanoparticles that encapsulate the bioactive agent.

Also provided by the present invention is a drug applicator comprising (i) an introducer having a drug-providing portion and (ii) means for passing an electrical current through said drug-providing portion, said introducer being adapted to penetrate into a living tissue, such that passing a current through said drug-providing portion when said introducer is inside said tissue and loaded with a charged drug, causes said drug to eject into said tissue.

A system comprising a drug applicator as disclosed above and a sponge suitable for use with said applicator is also provided by the present invention.

The present invention further provides a method for delivering a charged drug into a tissue, the method comprising inserting into said tissue a sponge loaded with said charged drug, and subjecting said sponge to an electrical potential gradient, such that at least part of said charged drug ejects into said tissue under said electrical potential gradient.

A sponge suitable for use in the above method, having dimensions that allow its insertion into a needle of 16-25 gage or its wrapping around such a needle, and is capable of absorbing and holding water in a weight that is at least 30% of its own weight, is further disclosed herein.

According to another aspect of the present invention there is provided a device for iontophoretic administration of charged drug to tissues of the oral cavity, said device comprising (i) an applicator, which is capable of conveniently accessing any point in the oral cavity, and includes a receiving portion adapted for holding a sponge in a manner allowing contact of said sponge with a surface of a tissue of the oral cavity and (ii) an electric current generating element, which is electrically coupled to the receiving portion of the applicator, such that once a current is generated, it passes through the sponge in a direction normal to the surface of the tissue of the oral cavity.

A system for the iontophoretic administration of charged drugs to a tissue of the oral cavity, comprising the above device and a sponge that is loaded with a charged drug and has size and shape accommodated with the receiving portion of the device, is also provided by the present invention.

The present invention additionally provides a method for the administration of charged drugs to a tissue of the oral cavity comprising contacting said tissue of the oral cavity with a sponge loaded with said charged drug; and passing a current through the sponge in a direction normal to the surface of said tissue.

DETAILED DESCRIPTION OF THE INVENTION

According to one aspect thereof, the present invention provides a device for iontophoretic administration of charged drug to tissues of the oral cavity. The device includes an applicator, which is capable of conveniently accessing any point in the oral cavity, and includes a receiving portion adapted for holding a sponge in a manner allowing its contact with a surface of the tissue of the oral cavity. The device of the invention further includes an electric current generating element, which is electrically coupled to the receiving portion of the applicator, such that once a current is generated, it passes through the sponge in a direction essentially normal to the surface of the tissue of the oral cavity.

The terms "essentially normal" or "normal", as used herein should be construed to mean that most of the charged drug moves under the influence of the electrical current from the receiving portion to the treated tissue.

The term "charged drugs" refers to pharmaceutical compositions which may be a priori charged, to drugs which become charged in a solution with which the sponge is loaded, as well as to drugs which are initially not charged but become charged in the presence of an electrical current.

The term "charged drugs" refers also to complexed bioactive agents, bioactive agents conjugated to smally or large molecules or polymers, and to bioactive agents encapsulated in a charged particle having a sub-micrometric size, whether the bioactive agent is charged or not.

Examples of commonly used charged drugs include antibiotics, such as gentamicin, tobramycin and vancomycin; antifungal drugs including miconazole, ketoconazole and omeprazol; anti-inflammatory agents such as ibuprofen and its derivatives, timolol; water soluble steroids such as dexamethasone phosphate and hydrocortisone succinate; anticancer agents such as mitomicin C, methotrexate and 5-fluorouracil; local anesthetics which are delivered to the oral cavity to anesthetize the gingival of tooth before a treatment or to reduce pain, such as lidocaine, bupivacaine and benoxinate.

The term "sponge" is used to denote a porous article made from hydrophilic or non-hydrophilic polymer, in which the porous structure allows it to absorb and hold at least 30% w/w aqueous solutions without dissolving or disintegrating.

Non-limiting examples to such non-hydrophilic polymers are polystyrene, polymethacrylates, silicones and urethanes.

Hydrophilic sponges, are termed herein hydrogel, and have functional groups that associate well with water molecules such as hydroxy, ether, amide, thiol, carboxylic acid, amine groups and the like. Non-limiting examples to such hydrophilic polymers are crosslinked hydroethylmethacrylate (HEMA) and other hydrophilic acrylate and methacrylate monomers, polyethylene glycol, crosslinked polysaccharides and proteins, and polyvinyl pyrrolidone. Swellable hydrophilic-hydrophobic copolymers such as HEMA-methyl methacrylate copolymers may also serve as sponge material.

A sponge loaded with a substance, is a sponge soaked or impregnated with that substance, in a manner that allows the sponge to release the substance at least under electrical field.

Charged nanoparticles may be formed from complexes of cationic and anionic macromolecules such as polylysine complex with plasmid DNA, antisense, peptides and proteins that form a charged complex with charged polymers that form cationic nanoparticles of a size in the range of 20 to 1000 nanometers. The degree of charge is dependent on the ratio between the polycation and the DNA. Preparation of polymeric nanospheres loaded with drugs is known from Nicoli et al., that reported nanospheres prepared from poly(lactide-glycolide) loaded with lidocaine or bupivacaine by coaservation or solvent evaporation. These nanospheres can be surface charged by including charged surfactants of fatty acid or amine which are incorporated in the surface of the nanospheres.

Charged nano-liposperes may be prepared by mixing solid triglycerides which is the active agent with charged phospholipids such as phosphatidyl ethanolamine for cationic charge or phosphatidylic acid for anionic charge. These lipid components are mixed with hot buffer in homogenization to form the charged nanoparticles loaded with the active agent.

The nanoparticles are loaded into the carrying sponge by absorption of a dispersion of the nanoparticles in the dry sponge. Suitable size of nanoparticles is 5 to 1000 nm in diameter, preferably between about 20 to about 200 nm. Larger particle size will move slowly in the gel. The smaller the particle is and the more charged it is, the movement of the particle within and out of the sponge and into the target tissue will be faster and more efficient.

As for the current generator of the device of the invention, the following characteristics may be mentioned:

The device includes an electrical current generating element which can be battery operated or connected to an external AC power source (DC power source may have also an application). The electrical current generating element is electrically coupled to the receiving portion of the applicator. In operation, when a sponge is fitted within the receiving portion, the electrical current generating element, generates currents that pass through the sponge in a direction substantially normal to the surface of the tissue of the oral cavity, thus causing the migration of charged drugs from the sponge to the tissue both due to electrical field as well as due to diffusion.

The current generator is preferably adapted to generate currents not higher than an upper limit which is preferably about 30 mAmps, more preferably about 5 mAmps.

According to one embodiment of the invention, the device includes an electric current control component for adjusting the level of electric current to pre-set levels. Preferably, such a device also includes a component allowing for fine-tuning of the level of electrical current produced by the electric current generating element of the device.

Typically, a device according to the invention has a ground element in the form of a wire extending externally from the device.

A device according to the invention may further include a timing element for activating the electric current generating element for pre-set period of time, and a switch for activating the timing element. The pre-set periods of time are preferably about 30 minutes or shorter, more preferably about 5 minutes or less.

Thus, in operation, the operator may choose a pre-set period of time, and a pre-set level of electric current (by adjusting the electric control element), and by mere activation of the switch, producing an electrical current of a fixed duration and level.

According to another embodiment of the invention the device has a switch which allows an electrical current as long as it is activated by the operator, but not longer than 5 minutes. This embodiment allows the operator to activate the device as long as he wishes according to the progression of the iontophoretic process and the reaction of the patient, and does not need to decide in advance on a treatment period.

The receiving portion of a device according to the invention is preferably formed with an indention for receiving a sponge, for example, an indention that is adapted to receive a cylindrical sponge.

According to another embodiment, the receiving portion is formed as a section of a ring or as a ring having an adjustable dimension.

The applicator may be held by a specific external fixing device, for example, during an operation to ensure its position, but preferably, for ease of handling, it should be hand held. The applicator may form a separate component of the device of the invention, or alternatively, the entire device of the invention may be in the form of a single instrument wherein the applicator is an integral part thereof. A key element of the device is a scaler-like rod having at its end, instead of a scaling means, a receiving portion such that a physician holding the scaler-like rod may conveniently access with the receiving portion having a drug-loaded hydrogel received therein, any site in the oral cavity.

The device provided by the present invention is accessible to the various locations in the oral cavity. Also, it is suitable for safe iontophoretic administration of drugs into the oral cavity and to sensitive tissues, which do not exceed pre-set periods and maximum level of electric current. The device of the invention enables safe reproducible and repeated administration of drugs to a specific area of a tissue.

According to another aspect of the present invention there is provided a system for the iontophoretic administration of drugs to a tissue of the oral cavity, comprising a device according to the invention and a sponge loaded with a drug and having a shape and size accommodated with the receiving portion of the device.

For example, where the receiving portion is conical or cylindrical, the sponge is in the form of conic or cylindric disc, respectively, having a size which precisely matches that of the receiving portion. Where the receiving portion is in the shape of a half ring the carrier is in the shape of a round disc. Preferably, the calibration size of the sponge should be in the size range of 0.2 mm to about 20 mm for administration to small regions, and preferably between about 3 to about 6 mm, for administration to the whole region of the inner mouth.

It is also possible to produce a system for iontophoretic administration of the oral cavity, wherein the receiving portion is adjustable, so that it can receive various sponges of various sizes, so that a single applicator is suitable for many sizes of sponges, for example the receiving portion may include a ring with an adjustable diameter which holds the sponge.

The hydrogel suitable for use in a system according to the invention typically has at least 30% of water (w/w). Non-limiting examples to the non-water components of such a hydrogel are hydroxyethyl methacrylate and crosslinking agents. The hydrogel may have any desired shape, non-limiting examples thereof are tubular, cylindrical, and conical shapes. The hydrogel's diameter is typically about 10 mm or less, even more typically about 3 mm or less.

According to another aspect of the present invention there is provided a method for the administration of charged drugs to a tissue of the oral cavity comprising contacting said tissue of the oral cavity with a sponge loaded with said charged drugs; and passing a current through the sponge in a direction normal to the surface of said tissue.

Non-limiting examples to tissues of the oral cavity that may be treated according to this aspect of the invention are gums, tooth, gingival, tongue, palate, and cheek. According to one embodiment, the drug is delivered to a teeth tissue through the gums.

The method according to the present invention is suitable for human and veterinary purposes.

The present invention further concerns topical delivery of herbal agents to an infected oral tissue or a lesion by iontophoretic applying a gel loaded with herbal active agents onto the lesion or infected oral tissue.

The present invention also concerns delivery of drugs to the roots of the tooth through the gingiva.

Another aspect of this invention concerns delivery of nanoparticles of non-charged drugs via iontophoresis. Suitable nanoparticles may be surface charged nanoparticles loaded with bioactive agents such as charged and non-charged molecules, peptides, protein and DNA.

Delivery of drugs encapsulated in biodegradable nanoparticles via iontophoresis provides controlled release of the encapsulated drug. Charged nanoparticles can be used for other purposes other than drug administration such as markers, electronic information and signatures.

By another aspect, the invention concerns a sponge for use in the above system, comprising a hydrogel material having at least 30%, and even above 50% w/w water content; the sponge being loaded with the charged drug of nanostructure. Preferably, such a sponge is a hydrogel.

The hydrogel material that is suitable for this application should contain at least 30% w/w of water to allow free transport of the drug through the gel; it should be compatible with mucosal tissue; be inert to the loaded drug and safe at storage and during application; it should not release any unwanted small irritating/toxic molecules; be stable during the life of the application; it should be physically and chemically stable in order to maintain its shape and size and its chemical and physical integrity; and generally should be comfortable in contact with mucosal tissue.

The hydrogel material is typically uncharged but may contain anionic (carboxylates) or cationic (amino groups) residues to enhance drug release upon application of a current pulse. The sponge may contain other organic or inorganic ions and salt solutions. Hydrogel discs are prepared from various known hydrogel compositions including: acrylic based hydrophilic monomers, crosslinked polysaccharides and polyols, and crosslinked polyethylene glycols. Various compositions of hydrogels were described by Dumitriu.

The charged drugs or nanoparticles are loaded into the sponge either during the preparation of the gel (for example during the polymerization process) or by placing a pre-prepared carrier pellet in a drug solution so that the gel absorbs the solution.

The present invention further relates to compositions and methods for treating or preventing diseases of the oral cavity in humans or animals, by applying to the oral cavity, a safe and effective amount of medications that have anesthetic, analgesic, antiviral, anti-inflammatory, anti-proliferative, antibacterial or antifungal activity. Of particular interest are local anesthetics including: bupivacaine, lidocaine, benzocaine, tetracaine, mepivacaine, prilocaine and etidocain; antimicrobials including: triclosan, chlorhexidine, erythromycin, povidone-iodine and gentamicine; antifungal like: amphotericin B, butoconazole, ciclopirox, nystatin, sulconazole, tolnaftate; anti-inflammatory agents like ibuprofen, indomethacin, ketoprofen, naproxen, piroxicam and tolmetin.

Herbal bioactive agents are also considered for administration by INT either directly for the charged compounds or after encapsulation in charged nanoparticles. Examples of active essential oils and plant extracts include: citronella oil, lemon oil, citron oil, cedarwood oil, juniper berries oil, lemon basis oil, rosmarinus offencinalis oil, cinnamon oil, cajuput oil, eucalyptus oil, fennel oil, geranium oil, girofle oil, lavender oil, clove oil, spearmint oil, myrte oil, oregano oil, pine oil, rosemary oil, sarriette oil, thyme oil, and tea-tree oil. Another group of active agents used in non-conventional medicine are the homeopathic agents which are usually charged and delivered in minute amounts.

The compositions and methods according to the present invention are suitable for treating or preventing diseases of the oral cavity in humans or animals, such as viral diseases herpes labialis (cold sores or fever blisters), herpes genitalis, herpes zoster (shingles), varicella zoster (chickenpox); inflammatory diseases and/or diseases demonstrating compromise or reaction of the immune system secondary to chemotherapy including aphthous stomatitis (canker sores) and oral mucositis (stomatitis).

Aphthous stomatitis lesions (canker sores) are characterized by the development of painful, recurring necrotizing ulcerations of the oral mucosa either as solitary or multiple lesions. Etiology is unclear; however, considerable evidence suggests the disease may be an immunologic hypersensitivity response to an L-form streptococcus bacterium. Precipitating factors in canker sore lesions may include trauma (dental procedures), self-inflicted bites (as in eating), endocrine changes (premenstrual period; following childbirth, menopause), acute psychological problems (period of increased stress), and allergic responses (asthma, eating certain foods or taking certain medications).

Oral mucositis (stomatitis), a common side effect of chemotherapy, may develop when chemotherapeutic agents sued to treat various neoplastic diseases interfere with the maturation and replication of the cells that comprise the oral epithelium. The condition may be focal or generalized and involve the buccal mucosa, palate, tongue, floor of the mouth and the gingiva. Oral mucositis is painful and as a result patients neglect oral hygiene and fail to maintain adequate nutrition and hydration. The compromised epithelial barrier can also facilitate invasion of potentially lethal bacteria and fungi that may lead to local infections and/or septicemia.

The present invention also provides a technique for delivering a charged drug into a body tissue using a sponge loaded with the charged drug and applying to it an electrical gradient, such that the charged drug moves into the tissue under the influence of the electrical field.

Thus, the present invention provides, in accordance with one of its aspects, a method for delivering a drug into a tissue, the method comprising inserting into said tissue a sponge loaded with charged drug containing said drug, and subjecting said sponge to an electrical potential gradient, such that said charged drug is ejected into said tissue under said electrical potential gradient.

Preferably, the method of the invention is carried out with a drug applicator comprising (i) an introducer having a drug-providing portion and (ii) means for passing an electrical current through said drug-providing portion, said introducer being adapted to penetrate into a living tissue, such that passing a current through said drug-providing portion when said introducer is inside said tissue and loaded with a charged drug, causes said drug to eject into said tissue.

The introducer may be, for example, a needle, catheter, or trocar.

According to one embodiment of the invention, the drug-providing portion is adapted to receive therein a sponge loaded with charged drug and designed to protect said sponge from squeezing. One such design may be of a cage-shape, which prevents squeezing of the sponge but allows the drug to be ejected upon application of electrical current.

According to another embodiment, the applicator is adapted to allow bringing to it a drug solution when the introducer is inside the tissue. Examples for mechanisms that allow bringing the solution when the introducer is inside the tissue are sponges that are saved in dry form in the tip of the introducer where shortly before introduction in the patient body or already when the tip is within the body, the solution of the drug is delivered via the introducer to the sponge. The drug solution may be introduced via the paving device, by a tube connected to the sponge within the paving device or outside thereof.

The term "paving device" is used herein interchangeably with the term "introducer", and as such may be, for example, a needle, a catheter, trocar, and the like.

In a further embodiment, the drug-providing portion includes a sponge loaded with charged drug and applied to the outer side of the applicator. The sponge may be dry, and in such a case it wets upon reaching the treated tissue, and then current is applied to eject the charged drug out from the wet sponge.

A dry sponge may be mounted inside the tip of the paving device prior to its insertion into the body or even the introducer may be manufactured with a drug loaded dry sponge. Alternatively, the sponge may be fixed to the outer side of the tip edge by suitable glue, which may be, for example, a sticky hydrogel such as polyvinyl pyrrolidone, carboxymethyl cellulose (CMC), poly(vinyl alcohol) or a rubber colloidal dispersion. It should be noted that the dry sponge may have the volume of the wet sponge or a smaller volume that upon absorption of water swells and expands to a predetermined volume. A sponge that is physically fixed or glued outside the introducer may have a shield protecting it from absorbing body-fluid on the way to the target tissue. Such a shield should eventually dissolve in the tissue, in order not to hinder the drug ejection into the tissue. The shield is preferably made of a material which is readily absorbable in the body, such as gelatin, oxidized cellulose, CMC, polyethylene glycol or other components used for similar purposes in the art of pharmaceutics and medical devices. Whether with or without such shielding, a sponge may be designed to ensure that its swelling rate is low enough to allow insertion to the delivery site without substantial swelling on the way.

A dry drug-loaded sponge may be prepared simply by swelling a sponge material with a suspension or solution of the drug, and drying the obtained sponge.

An intra-tissue drug delivery method and applicator as disclosed herein may have numerous applications in improving the intra-tissue distribution of drugs in the desired site. For example, in the case of solid tumors it is desired to deliver a large dose of drug intra-tumorally with even distribution of the drug so it treats each and every tumor cell. By using intra-tumoral iontophoresis, the charged drug or charged nanoparticles loaded with drug are ejected into the surrounding tissue to a certain distance upon application of a current. An iontophoretic probe with a controlled current and time of current application, may improve intra-tissue distribution.

The sponge can be loaded with the drug solution and then associated with the applicator or alternatively, it may be loaded with the drug solution when the introducer is already inside the body, for example, in the tissue to be treated. In both cases, it is possible to load the sponge with drug and eject out the drug by applying to it an electrical current more than once. The current applied can be up to about 20 miliAmper applied for up to about 30 minutes, preferably up to 5 miliAmper for about 5 minutes. The sponge may be left in the site of insertion if it is biodegradable such that it may eliminate safely with time. Non-degradable sponge may be bound to the introducer and removed from the site of insertion at the end of the procedure.

In the case where the drug loaded sponge is left behind in the tissue delivery site for further locally release of the drug, the sponge must be biodegradable and biocompatible and should also retain the loaded drug to ensure that the (non-iontophoretic) release of the drug is well determined. The sponge is detached from the applicator in the site of insertion by either mechanical means such as push out or pull off or by using a compatible glue that holds the sponge attached to the tip for a few minutes to allow iontophoretic introduction in the delivery site and then dissolves and releases the sponge. It is also possible that the sponge will be pushed-out of the device as a result of the swelling forces and its own volume increase.

The intra-tissue iontophoretic device of this invention may be used to deliver anticancer drugs to solid tumors such as tumors of the brain, prostate, column, breast, head and neck, sarcomas, liver, and other types of solid tumors. Anticancer agents including doxorubicine, methotrexate, 5-fluorouracil, platin derivatives, vinka alkaloids, taxanes and mitomycin C may be used either in free from or encapsulated in charged nanoparticles which may be, for instance, poly(lactide) or lipid based.

The device of this invention may be useful to deliver antimicrobial agents to site of intra-tissue infections such as in the case of soft tissue infections or bone infection (osteomyelitis). In the latter, the drug is delivered to the surface of the bone, to the bone, and the surrounding tissue. The device of the invention may also be used to prevent complications in surgical procedures with risks for infections, i.e. total hip replacement. Drugs such as antibacterial agent, i.e. aminoglycosides and penicillins, antifungal agents, i.e. polyene antibiotics, azol compounds, and antibacterial peptides and proteins, antiviral agents and antiparasites may be used for this purpose.

Another application of the invention may be in pain relief to deliver analgesic drugs to the site of pain and inflammation or local anesthetic close to peripheral nerves embedded in non-nerve tissue. Local anesthetics such as bupivacaine, lidocaine, and ligroine, antiinflammatroy agents such peroxicam, ibuprofen, dexamethasone phosphate or succinate, and indomethacine are some non-limiting examples for charged drugs that may be useful for this purpose.

According to another aspect of the present invention there is provided a method for delivering a drug, such as antibiotic, anti-inflammatory, anticancer agents, or analgesic agents, into a tissue exposed during a chirurgic procedure, the method comprising contacting said tissue with a sponge loaded with charged drug and passing an electrical current through said sponge.

In all the above description, contacting a sponge with a tissue should be construed as bringing the sponge and the tissue to a sufficiently proximate position, such that drug elected from the sponge may efficiently arrive to the tissue contacting it. This may be the case when there is a physical contact between the sponge and the tissue, but is not limited to such cases.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION OF THE DRAWINGS

Figure 1A:
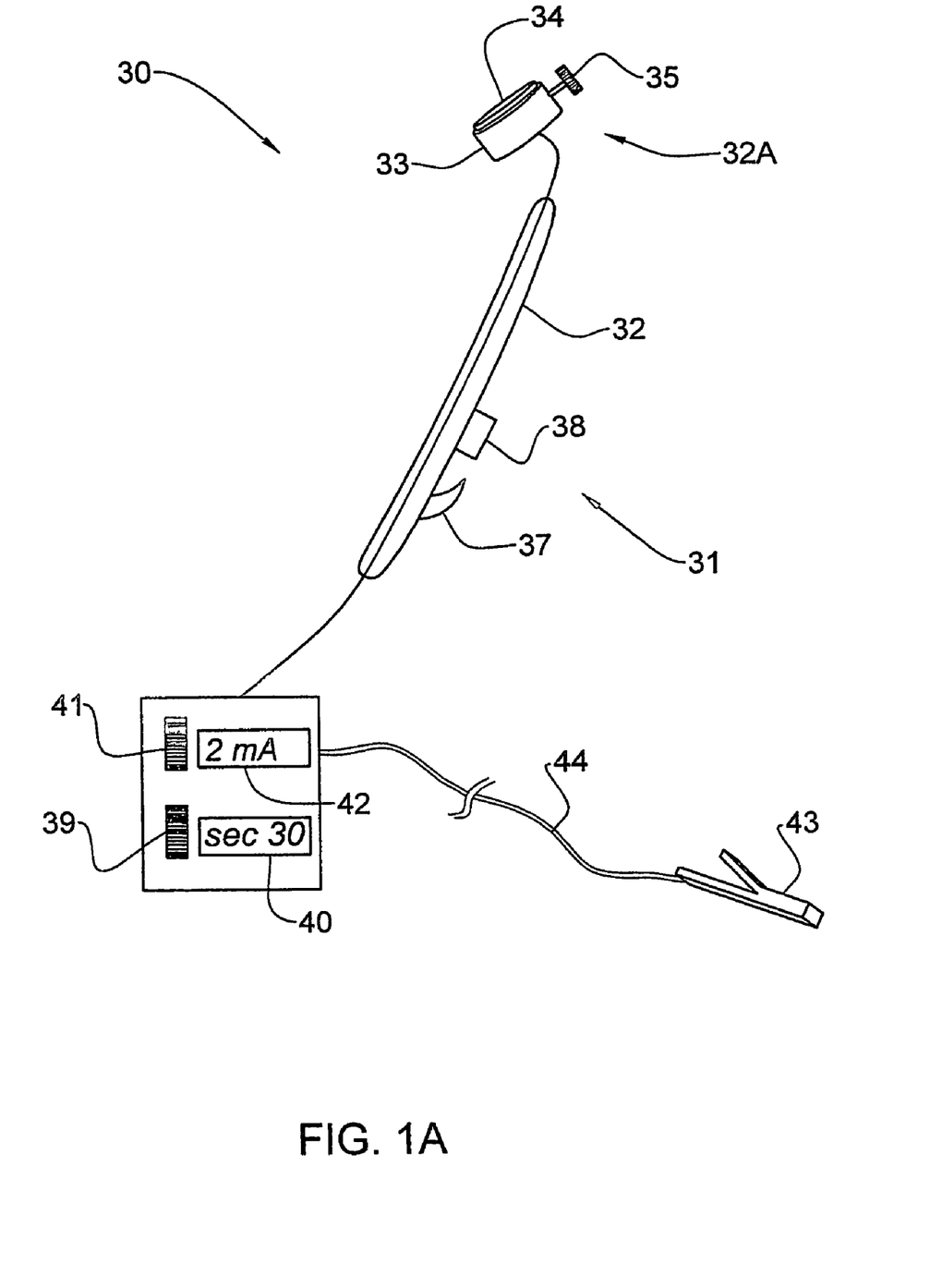
FIGS. 1A and 1B show schematic representations of two devices for INT to the oral cavity, both according to the invention.

Reference is now made to FIG. 1A, which shows a schematic representation of a device 30 according to the invention, when it is equipped with a hydrogel 34. The device 30 includes an applicator 31, which is capable of conveniently accessing any point in the oral cavity, and includes a receiving portion 32A adapted for holding a hydrogel carrier 34 in a manner allowing its contact with a surface of the tissue of the oral cavity (not shown).

The applicator 31 includes a curette-like arm 32 and an adjustable ring 33, which claps the hydrogel disc 34. The ring may accommodate hydrogel discs of various dimensions, by adjusting, with screw 35, the diameter of the ring.

The device 30 has an on/off switch 37, and a push button 38 which when pushed gives pulses of a pre-set length and current magnitude. In the embodiment shown in FIG. 1A, the switch 37 and push button 38 are associated with the curette-like arm 32, however, it may also be positioned differently, for instance, on the floor, to be operated by the dentist foot, as well known in the art of dentistry instrumentation.

The device has a time control button 39, a digital time display window 40, a current control button 41, and a digital current display window 42.

The counter-electrode 43 of the device 30 is connected to the device via wire 44.

In operation, the hydrogel 34 is placed onto the gingival or any other tissues in the oral cavity (not shown), and the counter electrode 43 is placed on any external part of the patient, for example, the ear, cheek, etc.

Figure 1B:
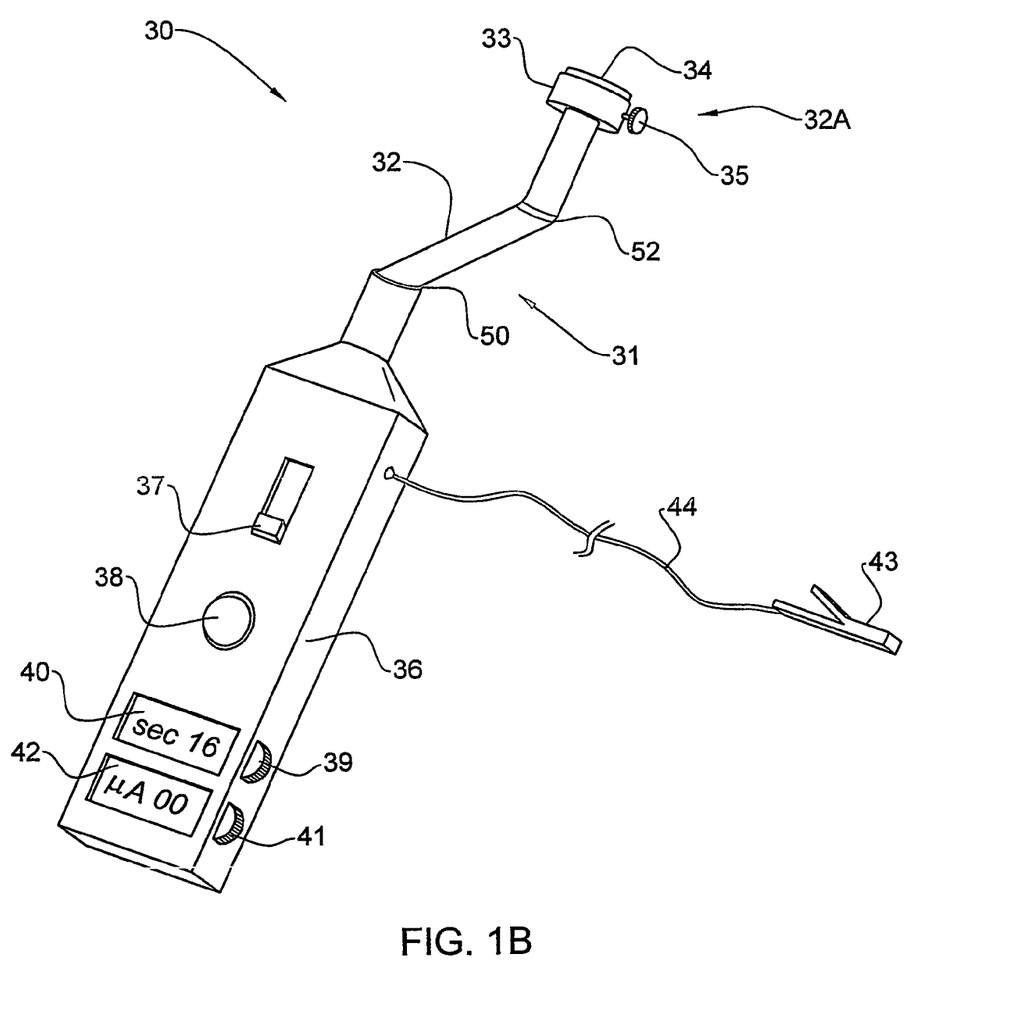
Figure 2A:
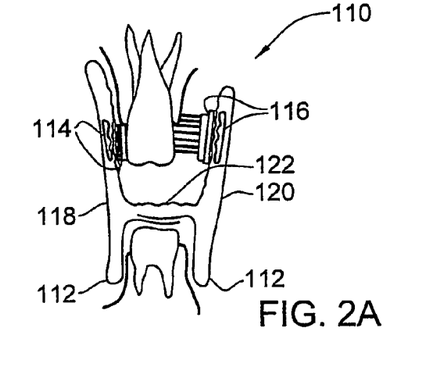
FIGS. 2A to 2F illustrate another embodiment of a device for INT to the oral cavity.
Figure 2B:
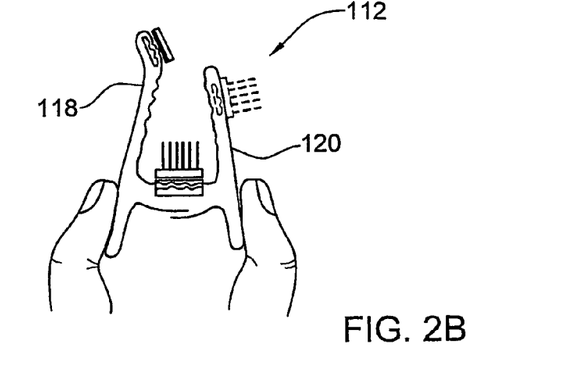
Figure 2C:
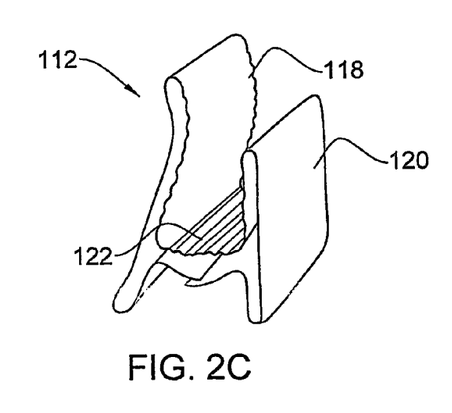
Figure 2D:
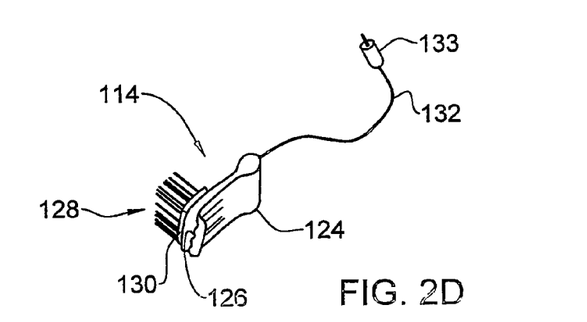
Figure 2E:
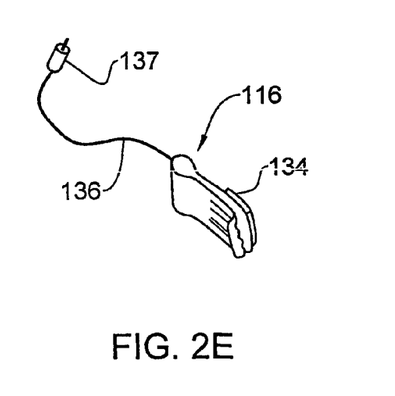
Figure 2F:
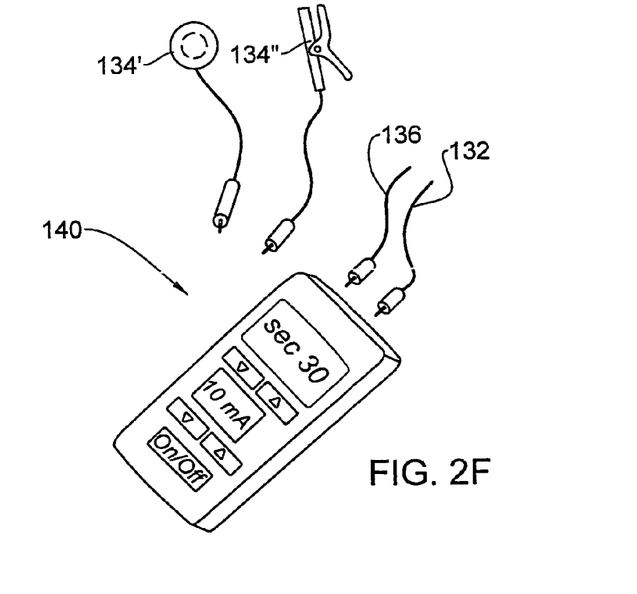

FIG. 1B shows another embodiment of the present invention, with similar parts referred to by similar numerals. The arm 32 of FIG. 1B has two joints 50 and 52, which allow positioning and fixing the arm in any required position, such that it may reach any point in the oral cavity.

To allow similar versatility, it is possible to manufacture the curette-like arm 32 of FIG. 1A from a flexible material, which may be bent to any desired shape, and retain this shape, such that it may reach any point in the oral cavity.

With reference to FIGS. 2A to 2F, the applicator 110 comprises a pincher 112, a gel clip 114, an electrode clip 116 and a control unit 140. The pincher 112 is bent (pressed) from a flexible strip of stainless steel in generally H-like shape with double walls, having vertical bars 118 and 120, and a horizontal bar 122. In a free state of the pincher, upper ends of the vertical bars 118 and 120 slightly converge. The walls of the pincher are corrugated for more reliable assembly of the clips 114 and 116, as explained below.

The gel clip 114 is also bent from a flexible strip 124 with corrugations 126 matching the ones in the pincher 112. The clip 114 carries an application brush 128 with conductive base 130 and an insulated conductor 132 with plug 133.

The electrode clip 116 has similar structure as the gel clip 114 but carries a contact pad 134 with insulated conductor 136 and plug 137.

The control unit 140 has controls and displays for setting and monitoring time and electric current values, and an ON-OFF button. The control unit 140 has receptacles (not shown) for plugs of the conductors 132 and 136.

In use, a quantity of medicine gel is applied to the brush 128, and the clips 114 and 116 are assembled in suitable positions to the walls of the pincher 112. Lower ends of the bars 118 and 120 are pressed so that the upper ends are opened, and the applicator is applied to a desired area of the teeth or gums. The cables 132 and 136 are plugged in the control unit 140. Then the control unit 140 is set and switched on.

The pincher 112 enables assembly of the gel clip 114 and the electrode clip 116 in various positions on its corrugated walls, including the horizontal bar 122 and an outward position (FIG. 2B), in dependence on the desired area for treatment. The H-like shape allows the opposite teeth on the other jaw of the patient to be used as a convenient support during treatment. The pincher may be also made of suitable plastic material, or with a spring-loaded hinge in the middle.

Instead of the electrode clip 116, another electrode with a contact pad 134' or 134" may be used as the passive electrode for application to a part of the body outside of the mouth cavity (i.e. on the skin of the cheek or on the ear, etc.)

Instead of the application brush 128, a porous pad may be used. Alternatively, a thimble-like hydrogel holder may be used.

A kit for iontophoretic treatment of the mouth cavity may include series of pinchers, gel clips, and electrodes with varying sizes and shapes.

Figure 3:
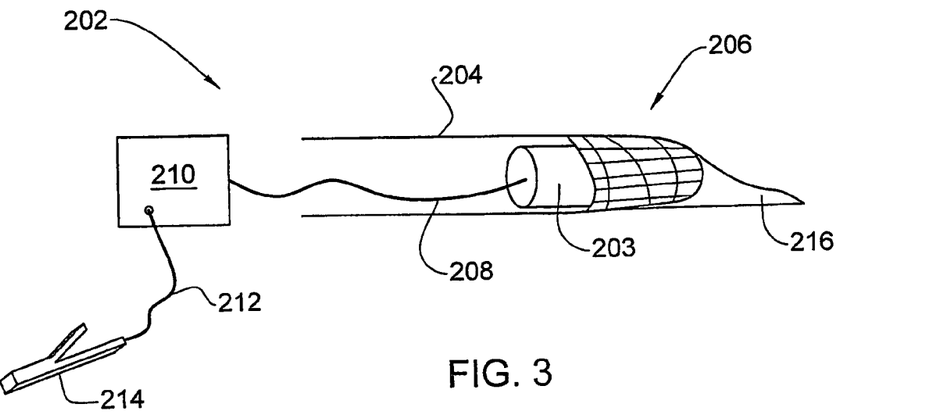
FIGS. 3 and 4 are schematic illustrations of two embodiments of intra-tissue drug applicators according to the invention.

FIG. 3 shows a schematic representation of a drug applicator 202 according to one embodiment of the invention, having in it a hydrogel 203 loaded with charged drug (not shown). The applicator 202 includes a needle 204, having a cage-like drug-providing portion 206 that protects the hydrogel 203 from squeezing, while allowing it to eject out the drug contained therein. The needle 204 also has a conductive wire 208, leading from the hydrogel 203 to a power source 210. From the power source 210 extends another wire 212 leading to a passive electrode 214, to be put on the patient skin to close the electrical circle. The tip 216 of the needle 204 may be open, like in conventional injection needle, or close, as in the drawing. In operation, the needle 204 penetrates into the tissue that should be treated (not shown), and the power source 210 is turned on to create a current through the drug-providing portion 206. This current causes the drug to eject out of the hydrogel 203 through the cage-like drug providing portion 206 into the tissue.

The needle 204 may be made of a metallic material, like many conventional injection needles, or from a plastic insulating material. If it is metallic, it should better be isolated from the wire 208 to prevent leakage of current through the needle and electrification of the patient.

Figure 4:
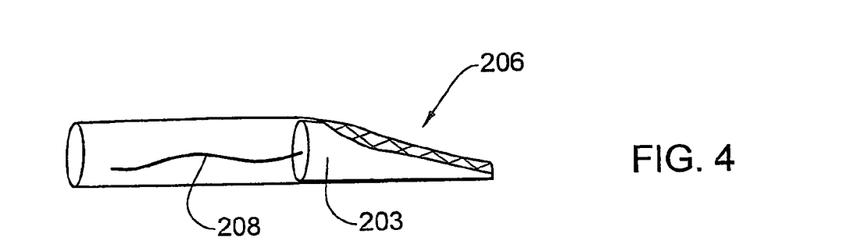

FIG. 4 shows a similar embodiment of the invention, wherein parts that are similar to those shown in FIG. 3 are referred by same numerals. The main differences between the embodiments of FIGS. 3 and 4 are that the drug-providing portion is located somewhat differently in the needle, and that the cage-like structure is built to allow ejecting of the charged drug in a preferred direction.

In the embodiments of FIGS. 3 and 4 the hydrogel 203 may be either dry or swelled prior to use. If the hydrogel is dry, a drug solution should first be flowed into the needle 204, and only after the hydrogel 203 is swelled, power is to turn on.

Figure 5A:
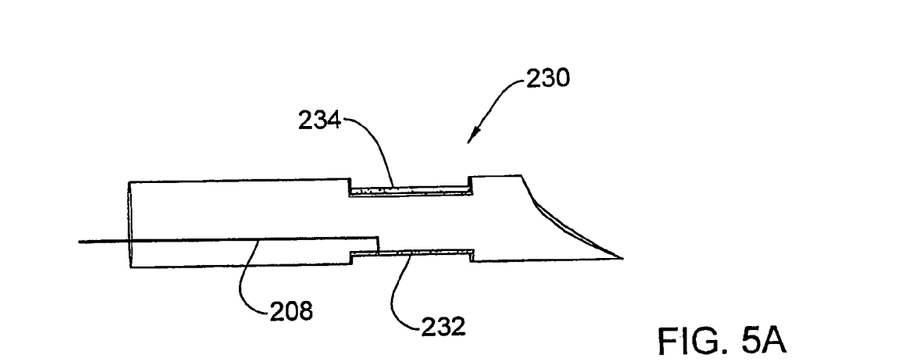
FIGS. 5A and 5B are schematic illustrations of another embodiment of the invention being an intra-tissue applicator with dry sponge (FIG. 5A) and swelled sponge (FIG. 5B).
Figure 5B:
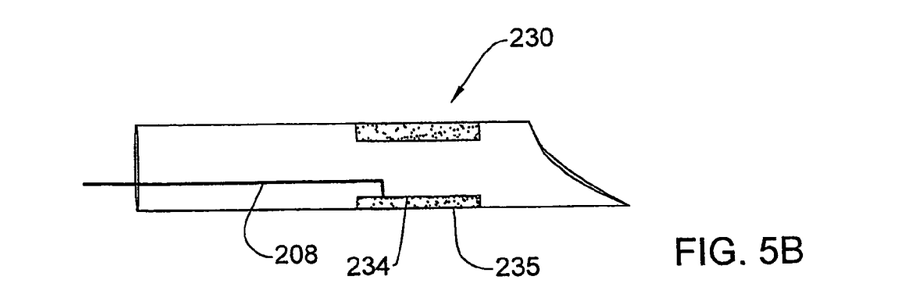

FIG. 5A shows another embodiment of the invention, where the drug-providing portion 230 has an indention 232 coated with dry gel 234 loaded with charged drug. The wire 208 is connected to the indention 232, which should be made of a conductive material. In FIG. 5B shown is the same embodiment when the gel 230 is wet. This wetness may be the outcome of contact with body fluid, or alternatively, the gel 234 may be swelled or fill the entire volume of the indention 232 prior to penetration into the body, in which case, it may be preferable to coat it with an absorbable shield 235. Dry gel loaded with drug may be prepared simply by swelling a gel material with a suspension or solution of the charged drug, and drying the obtained gel.

EXAMPLES

Example 1

Preparation of Disposable Hydrogel Loaded with Gentamicin Sulfate

The hydrogels were prepared by polymerization of solutions containing methylmethacrylate (MMA, 0-10%), hydroxyethylmethacrylate (HEMA, 3-50%), ethyleneglycol dimethacrylate (EGDMA, 0-5%), gentamicin (0-20%), water (20-95%) and a radical source (redox mixture, $Na_2S_2O_5$ and $Na_2S_2O_8$.) The solutions were cast between two flat glasses to form a film or into a Teflon mold and polymerized at room temperature overnight. The polymerized gels were cut into the appropriate size to fit the cavity of a probe.

Gentamicin was loaded into the gel either during polymerization of the monomers or by absorption from a 10% aqueous solution of gentamicin. Other useful uncharged monomers which may be used are acrylamide and its derivatives, N,N-ethylenediacrylamide, glycerol methacrylate, and N-vinylpyrrolidone. Charged monomers are methacrylic and acrylic acid, aminoethylmethacrylates, vinylpyridines and vinylimmidazoles.

In a typical preparation, HEMA (2.0 ml), EGDMA (0.04 ml), gentamicin sulfate (100 mg), water (2.0 ml) and a redox mixture of 2% w/v $Na_2S_2O_8$ (0.05 ml) and 2% w/v $Na_2S_2O_8$ (0.05 ml) are mixed to form a uniform solution. The solution was purged with dry nitrogen and then cast in between two flat glasses separated with a gasket of 2 mm and left to polymerize overnight at room temperature. The solid membrane was cut into circular discs of 3 mm in diameter.

Alternatively, the same polymer composition was prepared but without the drug and cast into a solid membrane of 2 mm thick. The membrane was cut into discs and the discs were dehydrated by lyophilization. The dried discs were allowed to hydrate into a 10% w/v gentamicin sulfate solution for 24 hours at room temperature. The hydrated discs were blotted with a sterile tissue prior to use. Gentamicin conjugated to dextran by an imine or amine bond may also be used as drug.

Other drugs such as lidocaine or bupivacaine hydrochloride, ibuprofen, chlorhexidine, dexamethasone phosphate or hydrocortisone acetate are loaded in the gel by first preparing solution of the drug in physiologic medium and then absorb the solution into the dry gel while swelling. These drugs can be incorporated in the polymerization solution to form the gel with the drug inside. The second method where drug free gels are prepared is preferred as it allows the purification of the gel prior to charge of the drug and it allows to use blank gel devices and load into them various drugs prior to use.

Similarly, drug loaded positively or negatively charged nanoparticles are loaded in the gels from an aqueous dispersion.

Example 2

Preparation of Polysaccharide Gels a. Albumin Cross Linking Oxidized Arabinogalactan (AG)

Albumin, a natural compatible protein containing amine groups, was reacted with increasing amounts of oxidized AG in order to obtain a cross-linked gel. The experiment was as follows: 1.0 gr. of egg-albumin (or bovine serum Albumin) was dissolved in 5.0 ml of 0.1 M $NaHCO_3$, the solution was incubated for 15 min. at 37° C. to obtain a clear-yellow solution which was reacted with a concentrated solution of oxidized AG (1.0 g in a 2 ml solution) for 24 hours at 37° C. to form an insoluble gel. Other proteins such as gelatin, chitosan, and collagen were also used instead of albumin.

b. Lysine Cross Linking with Oxidized Arabinogalactan 1.0 g of di-aldehyde Arabinogalactan (35% degree of oxidation) was dissolved in 4.0 ml deionized water and 25 mg of lysine hydrochloride was added to the polymer solution and the pH was adjusted to 8.0 using 0.1M NaOH solution. Under these conditions cross linking is fast. At the alkaline pH of the water phase, reaction of lysine with di-aldehyde Arabinogalactan proceeds rapidly and the gel hardened. The obtained gel was washed with water several times to remove soluble matters and dried in vacuum (yield=~90% by weight).

Reduction of the Imine-bond obtained in the gel was done by incubating the gel in sodium borohydride solution (1.5 mol $NaBH_4$ for each 1 mol sugar units of polysaccharide) for 4 hours at room temperature followed by filtration and washing with water. The reduced gel was placed in ethanol at 4° C. overnight, isolated and dried in vacuum. Gels with increased cross linking were obtained by reacting the oxidized polysaccharide with increasing amounts of lysine up to about 20% by weight per polymer. Other diamine molecules such as ethylene diamine, hexamethylene diamine and polyethylene imine can be used instead of lysine.

The dry gel was loaded with gentamicin by immersing the gel in a 10% gentamicin sulfate solution for 24 hours. Other drug solutions including herbal extracts and homeopathic agents were also charged in a similar way.

Example 3

Preparation of Polyurethane Gels

Polyurethane gel was prepared from Hypol PreMA G-60 (Hampshire Chem. Corp. Owensboro, Ky., USA) which is a reactive diisocyanate). The gel film was prepared by diluting the viscous Hypol in acetone (1 part in 2 parts) and then adding 2 parts of water. The solution was mixed well and the homogeneous solution was cast into a dye and allowed to solidify. The solution was solidified within 15 mins. and the polymerization was allowed to complete over night. The solid gel was placed in deionized water for 24 hours to extract impurities, cut into discs on 4×2 mm and then lyophilized. The clear and flexible dry discs were placed in a 10% by weight of gentamicin sulfate to absorb the solution and the hydrated gels were blotted with a paper tissue and weighed. The hydrated discs contained 92% of solution.

These discs are suitable for loading of charged drug-conjugates such as amphotericin B-conjugated arabinogalactan or dextran. Lipid nanospheres prepared from trilaurine core, phospholipid, stearyl amine, dispersed in water can be absorbed in the gels and used for iontophoresis administration to mucosal tissue.

Example 4

Preparation of Hydrogel Pellets Loaded with Drugs

Acrylic gel membranes prepared from cross-linked HEMA with 0.2-3% w/w of EGDMA or ethylenediacrylamide which absorb 85% of water. The membranes were freeze-dried to dryness following drug absorption/loading by immersing the polymer discs in 10% drug solutions in aqueous solutions (i.e. buffer solutions, mixtures of water with hydrophilic solvents such as alcohol, DMSO, DMF and THF) overnight. Loading of 5 to 50 mg drug/ml hydrated gel was obtained. The following drugs were incorporated into the acrylate gel: ibuprofen, fluoprofen, timolol, miconazole, pilocarpine, tobramycin, vancomycin, and peptides including LHRH and TRH.

Example 5

Homeopatic Drugs

A homeopathic medicine for use in the treatment of bacterial infections is prepared from the following ingredients: 77 drops of a 3× potency solution of a blend of bacterial detoxifying homeopathics, and 1 gallon of the homeopathic carrier solution which contains 1:9 alcohol:water. Seventy-seven drops of the 3× potency solution is added to a one gallon bottle. The one gallon bottle was then half filled with the homeopathic carrier solution of example 1 and the bottle is succussed by striking the bottle fifteen times on a leather-bound book. The bottle is then filled with the remainder of the homeopathic carrier solution and the bottle is again succussed by striking the bottle fifteen times on a leather-bound book. The homeopathic medicine is then ready for use. These solutions are charged into the gel and applied by iontophoresis.

Active agents that may be included in the formulation are: Aesculus hippocastanum extract, Arnica Montana extract, Belladonna, Echinacea angustifolia extract, Rhus toxicodendron extract, Ruta graveoleus extract, and Graphites at a typical concentration of 6 mcg/g and Crotalus horridus extract, Heloderma horridum extract, Lachesis extract, Naja extract and Mate extract at a typical concentration of 0.08 mcg/g. Solutions of the homeopathic agents were charged in the gels by immersing the dry gels in solutions of the homeopathis agent.

The advantages of the delivery of homeopathic agents via iontophoresis are: it avoids the need for multiple, repeat administrations in the course of the day at short intervals one from another; mono-administration and, above all, not having to hold the preparation under the tongue enormously facilitates patient compliance, particularly in the case of disabled persons, elderly patients and children; administration of the drug can be interrupted at any time it may be so desired; the administration is more effective owing to the slow release of the agent.

Example 6

Delivery of Nanoparticles to the Oral Cavity

Fluorescent labelled cationic charged nanoparticles were prepared by melt mixing of trimyristin (400 mg), Centrolex F (soy phospholipid) (100 mg), stearyl amine (50 mg), Nile red (a fluorescent hydrophobic dye, 2 mg), and an active agent (200 mg), To the melt, hot (50° C.) deionized water was added and the solution homogenized at a 20,000 rpm for 60 seconds while cooling in an ice bath. The nanodispersion had uniform positively charged particle of 60 nanometers particle size with cationic charge. Uncharged particulate formulation was prepared using the same procedure but without the stearyl amine. Anionic nanoparticles were similarly prepared but steric acid was substitute for steryl amine. The active agents that were loaded in the particles were: lidocaine, bupivacaine, dexamethasone phosphate, 5-FU, amphotericin B, paclitaxel and cyclosporin. The particle size of the particles in all formulations were in the range of 20 nm up to 200 nanometers. 200 microliter of the formulation was loaded in dehydrated 3×3 mm disc shape crosslinked HEMA gels and the hydrated gels were mounted onto the portable INT device. The gels loaded with 50 mg/ml cationic particles in deionized water, 50 mg/ml of non-charge particles, was applied on the gingiva of Sabra rats at two different places for each formulation at a current of 1 milliampere for 60 seconds. As control, the gels were applied onto the surface for 60 sec. The rats were sacrificed 10 minutes after administration and the treated tissues were removed for analysis. The tissues were sliced to a few micron thickness slices and each slice was detected by confocal microscopy for fluorescence. The cationic charged nanoparticles of 60 nanometer size penetrated to more that 1 mm within the tissue where the same sample but without current remain close to the tissue surface. Similar results were obtained when anionic nanoparticle were use operated with anionic current. When using 200 nanometers particle size dispersion, the penetration was less effective. Also, lower charge on the particles reduces the depth and intensity of the penetration. This experiment indicates the role of cationic charge particulate on enhancing nanoparticles into mucosal tissue.

Example 7

Iontophoretic Delivery of Gentamicin and Dexamethasone Phosphate to Rat Gingiva

Hydrogels loaded gentamicine sulfate (10% w/v) were applied onto the gingiva of Sabra rats as described in Example 6. The slices were analyzed for gentamicin content using the TDx Abbott system analysis. Significant amount of gentamicin was detected in the slices even at 1 mm thickness. The control experiment where no current was applied showed little penetration into tissue. In a similar experiment, dexamethasone succinate, a negatively charged antiinflammatory agent, was applied to the buccal using a negatively charged iontophoresis. Dexamethasone phosphate was determined by Hplc after reacting the tissue with a phosphatase enzyme that removes the phosphate group and the resulted hydrophobic dexamethasone was extracted from the minched tissue by ethyl acetate. Significant concentrations of dexamethason were found in the tissue.

Example 8

Delivery of Local Anesthetics to Gingiva

Flexible non-fragile cylindrical HEMA hydrogels (4×3 mm) loaded with 10% w/v of bupivacaine hydrochloride was prepared by immersing a dry crosslinked HEMA with 2% ethylene glycol dimethacrylate (EGDMA) in a 10% w/v bupivacaine solution for 3 hours at room temperature. The gel was mounted onto the iontophoretic device and the loaded apparatus was applied onto the gingiva of an adult and a current of 0.5 mA for 30 seconds was applied. The ejection site as well as the 2-5 mm surrounding area was anaesthetized to a level that pricking was not noticed by the patient. The same experiment was repeated onto the buccal and resulted with a strong anesthetic effect. The controls were, saline loaded hydrogels applied for the same time and current, or placement of the hydrogel without applying current. In both control experiments no anesthetic effect was noticed.

Example 9

Delivery of Drugs to Treat Gingivitis

Gingivitis is disease where pockets are formed between the gingival tissue and the surface of the tooth. This is caused usually by bacterial infection that penetrate into the space between the gum and the tooth. The current treatment is scaling or in severe cases a surgery where during these processes the infected bacteria is removed and the site is treated with antibiotics. The reason for scaling or surgery is the lack of way to deliver antibiotics within to the interface between the gum and tooth. In this experiment, a suspension of *Staf. Aureus* (1 million per ml) was injected into the space between the gingiva and the tooth of a rat and after sixteen hours, gentamicin was delivered to the site by iontophoresis applied onto the outer surface of the gum directly toward the infected area. A dose of 1 milliampere for 60 seconds onto a gel loaded with a 10% w/v solution of gentamicin sulfate was applied. After one hour, the animals were sacrificed and the tissues were take for bacterial count and gentamicin conytent in tissues. As reference, the gel was applied onto the gum for 60 seconds without applying current. The bacterial count for the gentamicin treated rats show levels in the range of thousands per gram tissue where the control animals show counts in the range of millions. These results were in accordance with the high levels of gentamicin found across the gingival tissue and into the tooth.

The invention claimed is:

1. A method for the administration of a bioactive to a tissue, comprising:

contacting the tissue with a sponge configured to absorb and hold at least 30% w/w of an aqueous solution without dissolving or disintegrating, the sponge loaded with the bioactive encapsulated in charged nanoparticles; and passing a current through the sponge in a direction that moves the bioactive towards the tissue.

2. The method according to claim 1, wherein the sponge is a hydrogel.

3. The method according to claim 1, wherein the bioactive agent is non-charged.

4. The method according to claim 1, wherein the nanoparticles have a diameter of between 20 and 200 nm.

5. The method according to claim 1, wherein the tissue is selected from the group consisting of solid tumor, internal tissue, mucosal tissue, and tissue of the buccal cavity.

6. The method according to claim 1, wherein the nanoparticles are formed from complexes of ionic macromolecules with charged polymers.

7. The method according to claim 1, wherein the nanoparticles are nano-lipospheres.

8. The method according to claim 1, wherein contacting comprises inserting into the tissue the sponge loaded with the bioactive encapsulated charged nanoparticles, such that at least part of the charged nanoparticles eject into the tissue under the current.

9. The method according to claim 8, wherein the tissue is a solid tumor.

10. The method according to claim 1, wherein the tissue comprises tissue exposed during a chirurgic procedure, and contacting comprises administering the nanoparticles into the tissue.

11. A sponge for administration to a tissue of charged nanoparticles encapsulating a bioactive agent, comprising:

a porous structure configured to absorb and hold at least 30% w/w of an aqueous solution without dissolving or disintegrating; and charged nanoparticles encapsulating a bioactive agent and being loaded in the porous structure, wherein the sponge is configured to come into direct contact with the tissue and to release the charged nanoparticles under an electrical field.

12. The sponge according to claim 11, wherein the nanoparticles have a diameter of from 20 to 200 nm.

13. A method for the administration of a bioactive to a tissue, comprising:

providing a dry sponge, configured to absorb and hold at least 30% w/w of an aqueous solution without dissolving or disintegrating, the dry sponge comprising a bioactive encapsulated in charged nanoparticles loaded in the dry sponge;

contacting the tissue with the dry sponge loaded with the bioactive whereby the sponge swells; and passing a current through the sponge in a direction that moves the bioactive towards the tissue.

14. A method for the administration of a bioactive to a tissue, comprising:
   providing a dry sponge, configured to absorb and hold at least 30% w/w of an aqueous solution without dissolving or disintegrating,
   swelling the dry sponge with an aqueous solution comprising a bioactive encapsulated in charged nanoparticles, to produce a swelled sponge loaded with the charged nanoparticles;
   contacting the tissue with the swelled sponge; and
   passing a current through the swelled sponge in a direction that moves the bioactive towards the tissue.

15. A sponge for administration to a tissue of charged nanoparticles encapsulating a bioactive agent, consisting of:
   a porous structure configured to absorb and hold at least 30% w/w of an aqueous solution without dissolving or disintegrating; and
   charged nanoparticles encapsulating a bioactive agent and being loaded in the porous structure,
   wherein the sponge is dry and is configured to come into direct contact with the tissue and to release the charged nanoparticles under an electrical field.

16. A sponge for administration to a tissue of charged nanoparticles encapsulating a bioactive agent, consisting of:
   a porous structure configured to absorb and hold at least 30% w/w of an aqueous solution without dissolving or disintegrating; and
   an aqueous solution comprising charged nanoparticles encapsulating a bioactive agent and being loaded in the porous structure,
   wherein the sponge is configured to come into direct contact with the tissue and to release the charged nanoparticles under an electrical field.

17. A drug applicator, comprising:
an introducer comprising
   a sponge configured to absorb and hold at least 30% w/w of an aqueous solution without dissolving or disintegrating, the sponge comprising charged nanoparticles comprising a bioactive, the charged nanoparticles being loaded in the sponge, and
   a drug-providing portion that holds the sponge, the drug-providing portion being configured to contact a living tissue such that the sponge is in direct contact with the living tissue, and release the charged nanoparticles under electrical current, the introducer being configured to penetrate into the living tissue, such that passing an electrical current through the drug-providing portion when the introducer holding the sponge inside the tissue, causes the nanoparticles to eject; and
means for passing the electrical current through the drug-providing portion.

18. The drug applicator of claim 17, wherein the sponge is a dry sponge.

* * * * *